United States Patent [19]

Colucci et al.

[11] 4,380,238

[45] Apr. 19, 1983

[54] DISPOSABLE APPLICATOR FOR MINI-LAPAROTOMY USING A CLIP METHOD

[75] Inventors: Bartholomew A. Colucci, Half Moon Bay, Calif.; Pierre Comte, Waldenburg, Switzerland

[73] Assignee: Institute Straumann, Waldenburg, Switzerland

[21] Appl. No.: 294,915

[22] Filed: Aug. 21, 1981

[51] Int. Cl.³ .............................................. A61B 17/00
[52] U.S. Cl. ...................................... 128/346; 128/325
[58] Field of Search ............... 128/346, 321, 323, 325; 81/416; 30/262

[56] References Cited

U.S. PATENT DOCUMENTS

| 72,735 | 12/1867 | Henry | 30/262 X |
|---|---|---|---|
| 2,635,238 | 4/1953 | Garland | 128/346 X |
| 3,270,745 | 9/1966 | Wood | 128/346 X |
| 3,926,195 | 12/1975 | Bleier et al. | 128/321 X |

FOREIGN PATENT DOCUMENTS 4684 of 1896 United Kingdom .................. 81/416

Primary Examiner—Stephen C. Pellegrino
Attorney, Agent, or Firm—Thomas E. Schatzel

[57] ABSTRACT

A disposable applicator device for applying tubal occlusion clips, particularly clips utilized in mini-laparotomy sterilization surgery. The applicator includes a grasping lever for grasping the hook portion of the clip and a guiding arm for gripping, guiding and forcing the projection portion of the clip. The grasping lever and guiding lever are connected by swivel hinge and a separation restrictor such that the relative motion of the levers is restricted to a predetermined arc within a plane. The applicator is adapted to deliver a tubal occlusion clip into position, force the clip from an open mode to a closed mode about the desired tissue, and then slidably disengage from the clip, leaving the clip installed upon the tissue.

7 Claims, 6 Drawing Figures

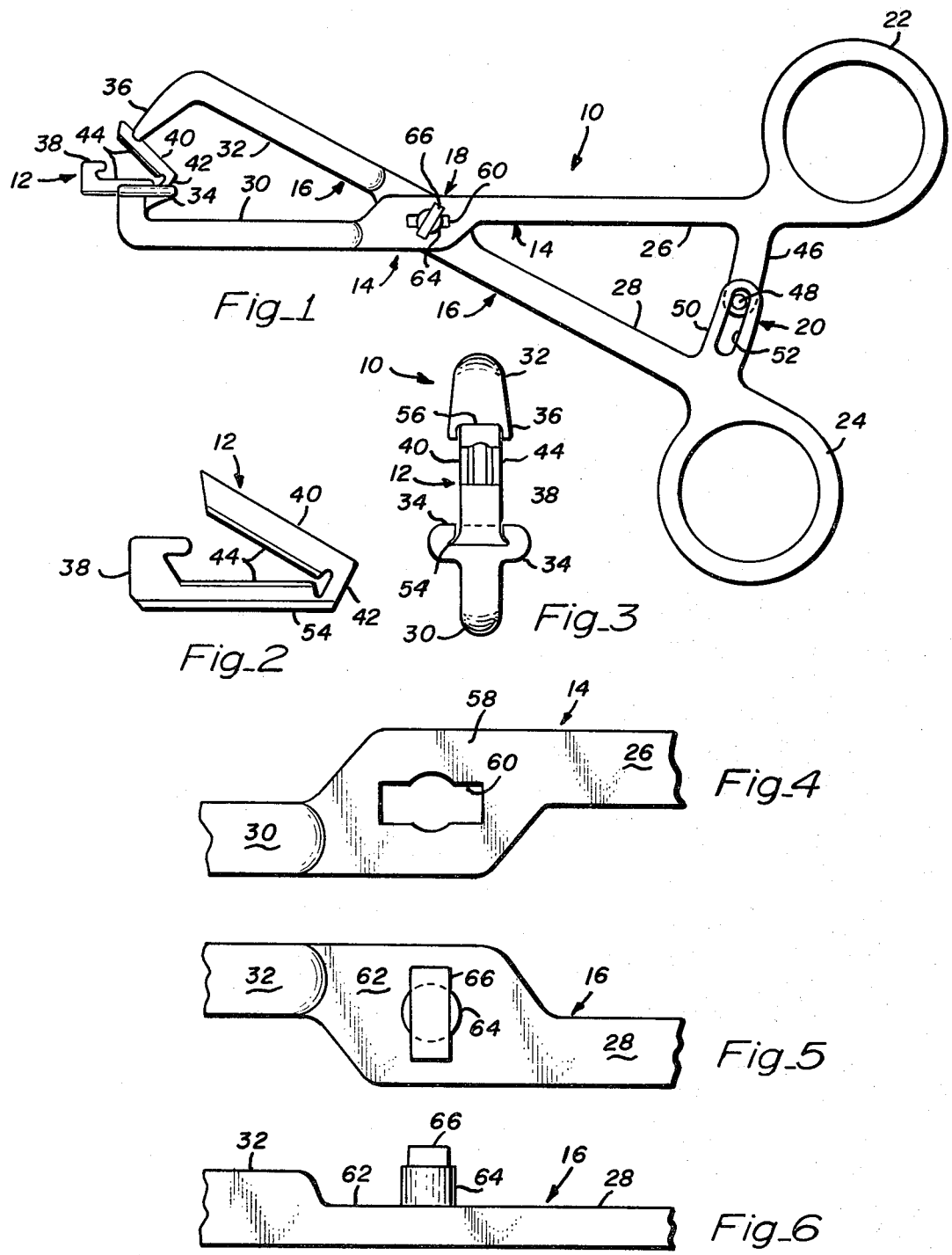

DISPOSABLE APPLICATOR FOR MINI-LAPAROTOMY USING A CLIP METHOD

BACKGROUND OF THE INVENTION

1. Field of the Invention

The present invention relates generally to surgical instruments and more specifically to instruments used to apply tubal occlusion clips.

2. Description of the Prior Art

As modern medical techniques have improved, very specific operational techniques have been devised for nearly every type of surgery. Since the various types of surgical operations required differ so widely and since great precision is required in each of these operations specific instrumentation has been developed for many different types and techniques of operations.

One type of surgery for which very specific instrumentation has been developed is female sterilization surgery. Female sterilization surgery is utilized to permanently, or in some occasions semi-permanently, eliminate the chances of a female becoming pregnant. Numerous surgical techniques have been developed for this purpose.

One of these surgical techniques utilized in female sterilization surgery is known as "mini-laparotomy". In one version of this surgical method the fallopian tube is closed by means of a clip device which is placed over the tube, occluding the tube such that the ova may not pass through the tube. This method of occlusion was primarily developed by Dr. W. Bleier of Germany. Consequently, a particular type of clip utilized to close the fallopian tube is called a Bleier clip.

The Bleier clip is the subject of U.S. Pat. No. 3,926,195, West German Pat. No. 1957855,22-20-117 and numerous other foreign patents, all issued to Dr. W. Bleier. The process which has been developed for utilizing the Bleier Clip for fallopian tube closure is described in a publication "Tube Closure By Means of Plastic Clip" distributed by Colmed LTD. of Burlingame, Calif.

One of the items of primary importance in a mini-laparotomy operation is the device utilized to apply the tubal occlusion clip to the tube. Various applicators have been designed for this purpose. One such applicator is described in the "Tube Closure" publication described above. Another type of applicator is a pistol grip type applicator which has been distributed in the United States by Colmed LTD. Each of these applicators has been designed for the purpose of holding a tubal occlusion clip of the Bleier clip variety for precise application to a fallopian tube. The applicators have been designed with the purpose of facilitating easy removal of the clip from the applicator.

All of the prior art applicators have been very complex devices with several parts. Both the pistol-grip-type, Colmed device and the original Bleier device involve multiple hinge mechanisms. Consequently, these devices are expensive and difficult to manufacture. Since the prior devices are very expensive to manufacture, it is economically unfeasible to make them disposable. Since subsequent sterilization of devices can be very time consuming, expensive and of questionable efficacy, there is a strong need for simplified and disposable devices.

SUMMARY OF THE INVENTION

It is therefore an object of the present invention to provide a simple, easy-to-use device for applying tubal occlusion clips.

It is a further object of the present invention to provide a device for applying tubal occlusion clips which is sufficiently economical to manufacture such that it may be used as a disposable device.

Briefly, a preferred embodiment of the present invention is a disposable applicator for applying a mini-laparotomy tubal occlusion clip. The applicator is constructed of a grasping lever and a guiding lever hingedly connected together in scissors fashion. The grasping lever is adapted to firmly hold the hook portion of a tubal occlusion clip in place while the guiding lever guides the projection portion of the clip into engagement with the hook portion. The applicator is also provided with a separation restrictor which limits the extent of the separation of the ends of the grasping lever and guiding lever so as to prevent the tubal occlusion clip from being either closed too tightly, thereby damaging the tissue, or opened too widely, thereby causing stress damage to the material of the clip.

It is an advantage of the present invention that the applicator device is very simple and may be easily manufactured such that it is economically feasible to utilize it as a disposable applicator.

It is a further advantage of the present invention that the degree of opening of the clip is sharply limited by the separation restrictor.

It is yet another advantage of the present invention that the applicator device is shaped in such a manner that it is easily utilized in the surgical area to which access is required in a mini-laparotomy operation.

These and other objects and advantages of the present invention will become apparent to those skilled in the art upon reading the detailed description of the preferred embodiment which is shown in the several figures of the drawing.

IN THE DRAWING

FIG. 1 is a side elevational view of a disposable applicator for a mini-laparotomy clip of the present invention, shown with a clip held within the applicator;

FIG. 2 is a side elevational view of a tubal occlusion clip for use in mini-laparotomy;

FIG. 3 is an end elevational view of the grasping lever and the guiding lever of the applicator of FIG. 1, shown with a the clip of FIG. 2 held in position;

FIG. 4 is a side elevational view of the interior hinge area of the grasping lever;

FIG. 5 is a side elevational view of the interior of the hinge area of the guiding lever; and FIG. 6 is a side elevational view, taken perpendicularly to the view of FIG. 5, of the hinge area of the guiding lever.

DETAILED DESCRIPTION OF THE PREFERRED EMBODIMENT

A preferred embodiment of the present invention is an applicator device for applying a tubal occlusion clip. The applicator is primarily used in the female sterilization operation known as mini-laparotomy. A preferred applicator is shown in the several figures of the drawing and is referred to by the general reference character 10. Applicator 10 is adapted for being used specifically with a clip element which is shown in the figures of the drawing and is referred to by the general reference character 12. The illustrated clip is generally referred to in the trade as a Bleier clip and marketed with the trademark Secuclip TM. Applicator 10 is specifically adapted for applying the clip 12 to a fallopian tube as an element of the mini-laparotomy surgical operation.

In FIG. 1, a side elevational view of the applicator 10 is shown with the applicator 10 holding a disengaged clip 12. It may be seen from this view that applicator 10 is formed of two separate elements which are hingedly affixed together. The first element is a grasping lever 14, a portion of which actually grasps the clip 12. The remaining element of the applicator 10 is a guiding lever 16 which lightly grips and guides the clip 12 from a disengaged to an engaged position.

The grasping lever 14 and the guiding lever 16 are connected by a swivel hinge means 18 near the center portions of the levers. Swivel hinge 18 functions to hold the levers together and further functions as a mutual fulcrum for the levers. The grasping lever 14 and the guiding lever 16 are further connected by a separation restrictor means 20 near the handle ends of the levers.

The grasping lever 14 is provided with a loop handle 22 at one end thereof. Similarly, the guiding lever 16 is provided with a loop handle 24 on the same end of guiding lever 16 as the loop handle 22 of the grasping lever 14. Loop handles 22 and 24 are adapted such that digital appendages of a surgeon may be inserted therethrough to manipulate the applicator 10.

Situated on the grasping lever 14, intermediate loop handle 22 and the swivel hinge means 18, is a grasping lever arm 26. Similarly, situated on the guiding lever 16, intermediate loop handle 24 and swivel means 18, is a guiding lever arm 28. Lever arms 26 and 28 intersect at the area of the swivel hinge means 18 and are connected at points displaced from the swivel hinge means 18 by the separation restrictor means 20.

Situated on the opposite side of the swivel hinge means 18 from grasping lever arm 26, and substantially linearly arrayed therewith, is a jaw arm 30. Similarly, situated substantially linearly across the swivel hinge means 18 from guiding lever arm 28 is a guide arm 32. In the embodiment 10 both the jaw arm 30 and the guide arm 32 are offset slightly such that their longitudinal axes are parallel to but not in conjunction with the longitudinal axes of lever arms 26 and 28, respectively. This offset is desirable for proper functioning of the swivel hinge means 18 and also such that a greater separation may be obtained between opposing points on jaw arm 30 and guide arm 32 than exists between similar points on the lever arms 26 and 28 at the same distance from the swivel point.

Jaw arm 30 culminates in a grasping jaw means 34. Grasping jaw means 34 is adapted for receiving and firmly grasping the clip 12 in the proper orientation for application to tissue such as an ovarian tube during surgical procedure. Guide arm 32 similarly culminates in a clip grip and guide means 36 which lightly grips the upper portion of the clip 12 and guides the clip from an open to a closed mode when the applicator 10 is properly manipulated. Clip grip and guide means 36 holds the clip 12 open to the desired extent until the applicator is closed.

Clip 12, as is more clearly shown in FIGS. 2 and 3, includes a hook portion 38 and a projection portion 40 which are connected at one end by an integral hinge 42 such that the projection portion 40 may rotate about the integral hinge 42 to an open position as shown or may snap lock into hook portion 38 in a closed mode. The opposing interior surfaces of hook portion 38 and projection portion 40 are provided with a plurality of complimentary ridges and valleys 44 such that any tissue held therebetween is deformed and compressed so as to conform to the contours of the ridges and valleys 44.

As illustrated in FIG. 1, the hook portion 38 of clip 12 is inserted into grasping jaw 34 and is held in position therein with a sufficient amount of freedom for integral hinge 42 to bend such that projection portion 40 may rotate a desired amount. Similarly, projection portion 40 is engaged with clip guide means 36. In the illustration of FIG. 1 clip 12 is shown in the open mode. However, when the applicator 10 is manipulated by moving loop handles 22 and 24 closer together such that grasping jaw means 34 and clip grip and guide means 36 are brought closer together the projection portion 40 will be snap locked into hook portion 38 such that clip 12 is in the closed mode.

As shown in phantom, grasping jaw 34 is closed at its interior end. This closed end limits the amount that a clip 12 may be slid into grasping jaw 34. In operation, the clip 12 is slid in against the closed interior wall of grasping jaw 34 such that the clip will be held in the same position and oriented for every usage of an applicator 10. The clip 12 may be easily removed from grasping jaw 34 by simply pulling the applicator 10 away from the clip 12 along the longitudinal axis of clip 12. Should sticking nonetheless occur, the clip 12 may be easily removed, since a portion of clip 12 extends above the grasping jaw 34 such that pressure applied to the back surface of integral hinge 42 will dislodge the clip 12 from the applicator 10.

The degree of separation of grasping jaw 34 and clip grip and guide 36 is important to prevent fatigue of integral hinge 42 should repeated flexing occur. This may occur if the clip 12 were allowed to open too fully. Additional advantage of a fixed position prior to application offers maximum opening for better utilization.

The separation restrictor means 20 of applicator 10 controls the degree of separation and assists in accomplishing these purposes. Separation restrictor means 20 includes a substantially planar post extension 46 extending from grasping lever arm 26 in the direction of guiding lever arm 28. Near the end of post extension 46 is formed a post 48 extending perpendicularly outward therefrom. A channel extension 50 including a channel 52 formed therein extends from guiding lever arm 28 such that it engages the post extension 46. Post 48 is adapted to fit into channel 52 and slide therein over the length of channel 52. Post extension 46, channel extension 50 and channel 52 are all curved in the shape of an arc of a circle having its center at the swivel point of applicator 10, which is located at the center of swivel hinge means 18. The motion of post 48 within channel 52 will be along this arc. Once installed therein, post 48 is restricted to movement within channel 52, such that applicator 10 may not be manipulated such that the arc of motion which post 48 traverses extends beyond either end of channel 52. The length of channel 52 is selected such that the resultant separation of grasping jaw 34 and clip guide 36 is such that at one extreme the clip 12 is held in an open position with no unnecessary stress upon integral hinge 42 while at the other extreme projection portion 40 is forced to snap lock with hook portion 38 but without unduly crushing the tissue held within clip 12.

Both the post extension 46 and the channel extension 50 are somewhat transversely flexible such that post 48 may be installed within channel 52 without disengaging swivel hinge means 18.

Referring now to FIG. 2, a Secuclip ™ version of a Bleier clip is shown in greater detail. This view illustrates the relationship between the hook portion 38, the projection portion 40 and the integral hinge 42. The ridges and valleys 44 which extend axially along the interior surfaces of both the hook portion 38 and the projection portion 40 may also be seen. This figure also illustrates that the hook portion 38 has, along its bottom, a pair of side wedges 54 which are utilized for stabilization of the clip 12 within the grasping jaw 34 (as shown in FIG. 3).

The end view of FIG. 3 illustrates the nature of the interaction between the clip 12 and the applicator 10. This view illustrates the precise interaction between the grasping jaw 34 and a pair of side wedges 54 of the hook portion 38 of the clip 12. The grasping jaw 34 is undercut slightly such that the clip 12 slidably fits into grasping jaw 34 but will not pull vertically out of the jaw.

FIG. 3 also illustrates the end portion of clip grip and guide means 36 which includes a depression 56 for receiving the upper surface of projection portion 40 of the clip 12. In the open position depression 56 lightly grips the projection portion 40 such that clip 12 is held open to the proper extent. The extent of opening will thus be the same for each applicator 10 having the same construction. Depression 56 also prevents the projection portion 40 from becoming laterally misaligned such that the opposing ridges and valleys 44 do not meet complimentarily with those of the hook portion 38. It is important to keep the clip portions properly aligned.

The mechanism of the swivel hinge means 18 is shown particularly in FIGS. 4, 5 and 6. It is important that swivel hinge means 18 create and maintain a firm connection between grasping lever 14 and guiding lever 16 such that any relative motion between the two levers is entirely within a single plane. This restriction is necessary to prevent the portions of clip 12 from becoming laterally disaligned.

FIG. 4 illustrates the construction of grasping lever 14 in the area of swivel hinge means 18. A flat planar surface 58 is formed on the side of grasping lever 14 which is to abut against the guiding lever 16. In the approximate center of planar surface 58 is formed a swivel aperture 60. The shape of aperture 60 is that of an elongated rectangle with a circle having a diameter slightly greater than the width of the rectangle situated about the center of the rectangle.

FIGS. 5 and 6 illustrate the complimentary structure on guiding lever 16 which form the remainder of swivel hinge means 18. Guiding lever 16 is also provided with a planar surface 62 for abutting against the planar surface 58 of grasping lever 14. Extending perpendicularly outward from planar surface 62 is a swivel pin 64. Mounted at the end of the swivel pin 64, and aligned perpendicularly thereto is a rectangular retaining bar 66. Retaining bar 66 is further aligned perpendicularly to the axis of guiding lever arm 28 and guide arm 32. The height of swivel pin 64 is selected to be very slightly greater than the thickness of the grasping lever 14 in the vicinity of aperture 60. Thus, the retaining bar 66 abuts relatively snugly against the exterior surface of grasping lever 14 when applicator 10 is assembled.

The applicator is constructed as follows. The grasping lever 14 and the guiding lever 16 are separately cast integral pieces. They are connected together by placing them with their longitudinal axes mutually perpendicular such that retaining bar 66 and swivel pin 64 slide through aperture 60. The levers are then swiveled about swivel pin 64 such that retaining bar 66 no longer fits through aperture 60. Once thus assembled, retaining bar 66 engages the outside surface of grasping lever 14 and holds the two levers in firm relationship to one another. Post 48 is then installed within channel 52 such that the separation restrictor means 20 will function properly. Once this assembly has been completed the only possible motion of the grasping lever 14 and the guiding lever 16 with respect to one another is in the plane of their rotation about swivel pin 64 and only over the arc defined by the allowed motion of post 48 within channel 52.

For the intended usage of applicator 10, the applicator is assembled and a clip 12 is installed within grasping jaw 34 in the open mode. The entire assembly is then sterilized and sealed in a sterile container, such as a sterile plastic bag. The sealed sterile assemblage may then be stored until such time as it is needed.

The structure and operation of applicator 10 lends it to construction out of medical grade plastics rather than metal. This construction minimizes costs to the point where it is economical to utilize the applicator as a disposable item. In this manner a surgeon may purchase an entire sterile assemblage and, after usage to install the clip 12 on the tissue, may simply dispose of the applicator 10. In this manner the necessity for intermediate sterilization is eliminated and the possibility of contamination during the step of inserting the clip within the applicator is removed.

Although the preferred embodiment is constructed of medical grade plastic there is no reason why any other suitable material may not be substituted. However, care must be taken that swivel hinge means 18 is sufficiently tight to prevent any lateral dislodgement and that separation restrictor means 20 be engageable and disengageable.

The applicator may be adapted for use with types of snap lock type clips other than the Secuclip ™ 12 merely by adjusting the shape and size of grasping jaw 34 and clip grip and guide means 36. The lengths of channel extension 50 and/or channel 52 may also be altered to accommodate different separation requirements.

A further embodiment of an applicator in accordance to this invention places the mutual fulcrum of the grasping and the guide levers at the end of the levers rather than in the middle. In such embodiment the levers form a forceps connection rather than the scissors shape illustrated. It is also possible to place the separation restrictor means 20 between jaw arm 30 and guide arm 32 rather than between grasping lever arm 26 and guiding lever arm 28.

Although described above in terms of the presently preferred embodiment the present invention is not to be construed as being limited to such embodiment. Those skilled in the art will no doubt observe various modifications and alterations which may be made in the device without exceeding the scope of the invention. Accordingly, it is intended that the disclosure not be construed as limiting and that the following claims be interpreted as including all devices which fall within the true spirit and scope of the invention.

We claim:

1. A disposable applicator for surgical tubal occlusion clips comprising:
   a grasping lever for holding a hook portion of a Bleier tubal occlusion clip firmly in position, said grasping lever including in a substantially linearly attached manner, a loop handle, a grasping lever arm, a hinge area, a jaw arm, and a grasping jaw means, said grasping jaw means being formed in a shape to slidably receive the hook portion of a tubal occlusion clip and to restrict the motion of the hook portion received therein except along the slide axis;
   a guiding lever for guiding and forcing a projection portion of said tubal occlusion clip from a disengaged mode to an engaged mode with regard to the hook portion, the guiding lever including, in a substantially linearly attached manner, a loop handle, a guiding lever arm, and a guide arm containing a depression at the end thereof for lightly gripping the projection portion of the tubal occlusion clip and guiding the projection portion from a uniform open position to a closed position;
   hinge means connecting the grasping lever and the guiding lever and providing a mutual fulcrum for the levers; and
   restrictor means interposed between the grasping lever and the guiding lever for limiting both the maximum and minimum separation of the hook portion and said projection portion of the tubal occlusion clip held therebetween.

2. The applicator of claim 1 wherein
   the hinge means connects the grasping lever and the guiding lever in scissors fashion.

3. The applicator of claim 2 wherein
   the separation restrictor means is situated on the opposite side of the hinge means from the clip holding portion of the grasping lever.

4. The applicator of claim 2 wherein
   the hinge means includes a first planar surface formed on the central interior side of the grasping lever and having a swivel aperture formed therethrough, a second planar surface formed on the interior side of said guiding lever opposing said first planar surface, said second planar surface having a swivel pin extending perpendicularly therefrom for extending through said swivel aperture, and a retaining bar formed at the end of said swivel pin for fitting through said swivel aperture in at least one orientation and for holding the grasping lever and the guiding lever in planar relationship.

5. The applicator of claim 4 wherein:
   the separation restrictor means includes a post extension extending from said grasping lever arm, said post extension having a perpendicular post extending therefrom, and a channel extension extending from said guiding lever arm, said channel extension having a channel formed therethrough for receiving said post.

6. The applicator of claim 1 wherein
   said grasping lever arm is aligned parallel to but offset from the axis of said jaw arm and said guiding lever arm is aligned parallel to but offset from the axis of said guide arm.

7. The applicator of claim 1, wherein,
   said applicator is constructed of medical grade plastic.

* * * * *